US008175350B2

(12) United States Patent
Suri et al.

(10) Patent No.: US 8,175,350 B2
(45) Date of Patent: May 8, 2012

(54) METHOD FOR TISSUE CULTURE EXTRACTION

(75) Inventors: Jasjit S. Suri, Roseville, CA (US); Liyang Wei, Grass Valley, CA (US); Dinesh Kumar, Grass Valley, CA (US)

(73) Assignee: Eigen, Inc., Grass Valley, CA (US)

(*) Notice: Subject to any disclaimer, the term of this patent is extended or adjusted under 35 U.S.C. 154(b) by 1058 days.

(21) Appl. No.: 12/014,635

(22) Filed: Jan. 15, 2008

(65) Prior Publication Data

US 2008/0170770 A1 Jul. 17, 2008

Related U.S. Application Data

(60) Provisional application No. 60/884,941, filed on Jan. 15, 2007.

(51) Int. Cl.
*G06K 9/62* (2006.01)
(52) U.S. Cl. ........ 382/128; 382/130; 382/131; 382/132; 128/922; 600/407; 600/416; 600/437; 600/438; 600/458; 702/19; 702/20; 702/21
(58) Field of Classification Search .................. 382/128, 382/130, 131, 132; 128/922; 600/407, 416, 600/437, 438, 442, 458; 702/19, 20, 21
See application file for complete search history.

(56) References Cited

U.S. PATENT DOCUMENTS

| | | | |
|---|---|---|---|
| 5,224,175 A * | 6/1993 | Gouge et al. | .............. 382/128 |
| 5,282,472 A | 2/1994 | Companion et al. | |
| 5,320,101 A | 6/1994 | Faupel et al. | |
| 5,383,454 A | 1/1995 | Bucholz | |
| 5,398,690 A | 3/1995 | Batten et al. | |
| 5,454,371 A | 10/1995 | Fenster et al. | |
| 5,531,520 A | 7/1996 | Grimson et al. | |
| 5,562,095 A | 10/1996 | Downey et al. | |
| 5,611,000 A | 3/1997 | Szeliski et al. | |
| 5,810,007 A | 9/1998 | Holupka et al. | |
| 5,842,473 A | 12/1998 | Fenster et al. | |
| 6,092,059 A | 7/2000 | Straforini et al. | |
| 6,171,249 B1 | 1/2001 | Chin et al. | |
| 6,238,342 B1 | 5/2001 | Feleppa et al. | |
| 6,251,072 B1 | 6/2001 | Ladak et al. | |
| 6,261,234 B1 | 7/2001 | Lin | |
| 6,298,148 B1 | 10/2001 | Cline et al. | |

(Continued)

FOREIGN PATENT DOCUMENTS

WO 0014668 3/2000

(Continued)

*Primary Examiner* — David A Vanore
*Assistant Examiner* — Nicole Ippolito
(74) *Attorney, Agent, or Firm* — Marsh Fischmann & Breyfogle LLP

(57) ABSTRACT

An image guidance system is provided for improving tissue culture extraction where the tissue is extracted under the guidance of first and second knowledge-based systems. The first knowledge-based system provides initial suggested regions of interest for tissue biopsy in an internal organ. These regions of interest are then confirmed as being of interest of being benign by the second knowledge-based system. Information from two different sources may provide a more accurate, intelligent and robust method that helps in selecting biopsy sites accurately, such that suspicious regions are not overlooked and the benign regions are not unnecessarily operated upon. This not only helps in better diagnosis and treatment, but also helps reduce pain to the patient, in addition to reducing wastage of resources and invaluable time.

7 Claims, 15 Drawing Sheets

U.S. PATENT DOCUMENTS

| | | |
|---|---|---|
| 6,334,847 B1 | 1/2002 | Fenster et al. |
| 6,342,891 B1 | 1/2002 | Fenster et al. |
| 6,351,660 B1 | 2/2002 | Burke et al. |
| 6,360,027 B1 | 3/2002 | Hossack et al. |
| 6,385,332 B1 | 5/2002 | Zahalka et al. |
| 6,423,009 B1 | 7/2002 | Downey et al. |
| 6,447,477 B2 | 9/2002 | Burney et al. |
| 6,500,123 B1 | 12/2002 | Holloway et al. |
| 6,561,980 B1 * | 5/2003 | Gheng et al. .................. 600/443 |
| 6,567,687 B2 | 5/2003 | Front et al. |
| 6,610,013 B1 | 8/2003 | Fenster et al. |
| 6,611,615 B1 | 8/2003 | Christensen |
| 6,674,916 B1 | 1/2004 | Deman et al. |
| 6,675,032 B2 | 1/2004 | Chen et al. |
| 6,675,211 B1 | 1/2004 | Mamaghani et al. |
| 6,689,065 B2 | 2/2004 | Aksnes et al. |
| 6,778,690 B1 | 8/2004 | Ladak et al. |
| 6,824,516 B2 | 11/2004 | Batten et al. |
| 6,842,638 B1 | 1/2005 | Suri et al. |
| 6,852,081 B2 | 2/2005 | Sumanaweera et al. |
| 6,909,792 B1 | 6/2005 | Carrott et al. |
| 6,952,211 B1 | 10/2005 | Cote et al. |
| 6,985,612 B2 | 1/2006 | Hahn |
| 7,004,904 B2 | 2/2006 | Chalana et al. |
| 7,008,373 B2 | 3/2006 | Stoianovici et al. |
| 7,039,216 B2 | 5/2006 | Shum et al. |
| 7,039,239 B2 | 5/2006 | Loui et al. |
| 7,043,063 B1 | 5/2006 | Noble et al. |
| 7,095,890 B2 | 8/2006 | Paragios et al. |
| 7,119,810 B2 | 10/2006 | Sumanaweera et al. |
| 7,139,601 B2 | 11/2006 | Bucholz et al. |
| 7,148,895 B2 | 12/2006 | Konishi et al. |
| 7,155,316 B2 | 12/2006 | Sutherland et al. |
| 7,162,065 B2 | 1/2007 | Ladak et al. |
| 7,167,760 B2 | 1/2007 | Dawant et al. |
| 7,225,012 B1 | 5/2007 | Susil et al. |
| 7,274,811 B2 | 9/2007 | Sirohey et al. |
| 7,302,092 B1 | 11/2007 | Fenster et al. |
| 7,403,646 B2 | 7/2008 | Sato |
| 2003/0000535 A1 | 1/2003 | Galloway, Jr. et al. |
| 2003/0135115 A1 | 7/2003 | Burdette et al. |
| 2004/0210133 A1 | 10/2004 | Nir |
| 2005/0159676 A1 | 7/2005 | Taylor et al. |
| 2005/0190189 A1 | 9/2005 | Chefd'hotel et al. |
| 2005/0197977 A1 | 9/2005 | Buck et al. |
| 2005/0243087 A1 | 11/2005 | Aharon |
| 2005/0249398 A1 | 11/2005 | Khamene et al. |
| 2006/0002601 A1 | 1/2006 | Fu et al. |
| 2006/0002630 A1 | 1/2006 | Fu et al. |
| 2006/0013482 A1 | 1/2006 | Dawant et al. |
| 2006/0036162 A1 | 2/2006 | Shahidi et al. |
| 2006/0079771 A1 | 4/2006 | Nir |
| 2006/0197837 A1 | 9/2006 | Flath et al. |
| 2006/0227131 A1 | 10/2006 | Schiwietz et al. |
| 2006/0258933 A1 | 11/2006 | Ellis et al. |
| 2007/0014446 A1 | 1/2007 | Sumanaweera et al. |
| 2007/0040830 A1 | 2/2007 | Papageorgiou |
| 2007/0116339 A1 | 5/2007 | Shen |
| 2007/0116381 A1 | 5/2007 | Khamene |
| 2007/0189603 A1 | 8/2007 | Kasperkiewicz et al. |
| 2007/0201611 A1 | 8/2007 | Pratx et al. |
| 2007/0270687 A1 | 11/2007 | Gardi et al. |
| 2008/0002870 A1 | 1/2008 | Farag et al. |
| 2008/0123910 A1 | 5/2008 | Zhu |
| 2008/0123927 A1 | 5/2008 | Miga et al. |
| 2008/0170770 A1 | 7/2008 | Suri et al. |
| 2008/0247616 A1 | 10/2008 | Pescatore et al. |
| 2009/0093715 A1 | 4/2009 | Downey et al. |
| 2009/0226065 A1 * | 9/2009 | Chen ............................ 382/131 |
| 2010/0098306 A1 * | 4/2010 | Madabhushi et al. ......... 382/128 |

FOREIGN PATENT DOCUMENTS

| | | |
|---|---|---|
| WO | 2006089426 A1 | 8/2006 |
| WO | 2008062346 A1 | 5/2008 |
| WO | 2008124138 A1 | 10/2008 |

* cited by examiner

METHOD FOR TISSUE CULTURE EXTRACTION

CROSS REFERENCE TO RELATED APPLICATIONS

This application claims priority under 35 U.S.C. §119 to U.S. Provisional Application No. 60/884,941 entitled: "An Improved Method For Tissue Culture Extraction" having a filing date of Jan. 15, 2007, the entire contents of which is incorporated by reference herein.

FIELD

The present invention relates to medical imaging. One aspect is directed to image guided surgery using a first knowledge-based system to identify regions of interest for biopsy and using a second knowledge-based system to confirm such regions as being desirable for biopsy.

BACKGROUND OF THE INVENTION

Prostate cancer is the most common type of cancer found in American men, other than skin cancer. According to American Cancer Society, there will be about 234,460 new cases of prostate cancer in the United States in 2006 and about 27,350 men will die of this disease. Prostate cancer is only curable at an early stage. Therefore, early detection is extremely important to reduce mortality and enhance the cure rate.

Current screening for prostate cancer relies on digital rectal examination and prostate specific antigen (PSA) value measurement. And definitive diagnosis of prostate cancer is based on histological tissue analysis. This is most often obtained via needle biopsy, guided by transrectal ultrasound (TRUS). Currently biopsy is the only way to confirm the diagnosis of the prostate cancer. During a biopsy an urologist obtains tissue samples from the prostate. A biopsy gun inserts the needle into the prostate and removes the tissue sample in less a second. However, in TRUS-directed biopsies, tissue sampling within different sections is done in a random fashion, since no prior information about the spatial location of the cancer is available. Normally, urologists divide the left and the right parts of the prostate into 3 regions each and randomly sample each of them. This not only causes pain to the patient (55% of men report discomfort during prostate biopsy), but also decreases the accuracy of the method (this method has shown to have a large false negative detection rate ranging from 27% to 39%).

SUMMARY OF THE INVENTION

Provided herein are systems and methods (i.e., utilities) that allow for providing an image guidance system that uses two knowledge-based systems for improving the tissue culture and workflow for urologists. The utility not only uses one knowledge-based system to provide guidelines for biopsy site selection, but also confirms the confidence in site selection through another knowledge-based system. In this regard, the utilities may be implemented in processing systems that are integrated into medical imaging devices and/or that are interconnected to the medical imaging devices and operative to receive data there from. The ability to select and confirm biopsy site selection reduces the need to sample non-suspicions regions and thereby reduces patient discomfort while improving biopsy accuracy. Further such a utility may be performed on-line, for example while a patient remains in view of an imaging device. Accordingly, this may allow for guidance to one or more biopsy sites of interest without repositioning the patient.

Another relates method is to use a knowledge-based system to guide tissue culture extraction. The acquired data is then fused using multi-modality image data set or warped using a knowledge-based system such as an ATLAS. But a knowledge-based system may only be used as a guideline in the absence of a validation/confirmation system. The present invention presents a new image guidance system for performing biopsy which can overcome the above-referenced problems and improve prostate cancer diagnosis. In presented utility, the suggested biopsy locations from a knowledge-based system are confirmed by another knowledge-based or learning based system such that higher confidence level can be established in selecting the biopsy sites.

In accordance with one aspect, a utility is provide where a first knowledge-based system is combined with a second knowledge based system together in the image guidance system. Initial regions of interest in the prostate are determined by the first knowledge-based system. Then the second knowledge-based or learning-based system is used as a "confirmation sub-system" to confirm that the regions of interest are suspicious and whether the tissue should be extracted form those regions.

In one arrangement, the first knowledge-based system is a statistical atlas of spatial distributions of prostate cancers that is constructed from histological images obtained from radical prostatectomy specimens. In such an arrangement, biopsy strategies or statistical information generated in the atlas space may be mapped to a specific patient space such as a portion or all of a prostate image in order to identify initial regions of interest without confirmation. The second knowledge-based can check those initial regions of interest found by the first knowledge-based system and classify whether they are, for example, potentially malignant or cancerous or healthy. This is the confirmation procedure to improve tissue culture extraction procedure. In one arrangement, these systems are on-line systems that are operative to suggest and confirm regions of interest during a patient procedure.

In one arrangement, the second knowledge-based system may perform an image textural analysis and classification for the initial regions of interest. The confirmation procedure may confirm whether the selected target has textural characteristics or other features that are similar to the textural characteristics and or features of histological samples having one or more classified malignancies, tumors and/or cancers. In one arrangement, feature vectors are extracted from the regions of interest by image processing algorithms. The feature vectors may include, without limitation, statistical features, gradient features and/or Gabor filtering features. Features with the most discriminant power may selected through a feature selection algorithm. Further multiple features may be selected for each region of interest. As a result, multiple features from each region may be compared with predetermined features associated with known cancerous, malignant and/or benign histological samples. Where multiple regions of interest are considered, multiple features are extracted and/or multiple features are compared, processing may be performed in parallel processing paths to reduce the processing time required to confirm one or more regions of interest.

In accordance with another aspect a system and method (i.e., utility) for training and utilizing a biopsy site confirmation system is provided. The utility may include the following steps, without limitation: (1) generating tumor ground truth locations or regions; (2) extraction of information known to the tumor region (e.g., feature extraction); (3) feature selection; and/or (4) classifier training. The following steps may be included in the online classification procedure of the biopsy site confirmation utility: (1) extracting information known to the suggested biopsy regions (ROIs) which provided by a first knowledge-based system; and/or (2) classification and confirmation of the regions of interest using trained classifier. The classification system may be an online system and can achieve real-time to assist urologists in prostate cancer diagnosis. The multi-threading technique and multi-resolution technique are designed in the workflow.

The overall utility including offline and on-line portions, which are considered novel alone as well as in combination, can be summarized as follows: first, in a training dataset, the 3D image volumes are mounted into 2D image slices. Organ boundaries in each 2D image slice may be segmented, by a semi-automatic or automatic segmentation algorithm. Histology data with tumor regions marked out by urologists may be registered to the 2D slices by a registration procedure. In one arrangement, tumor regions in histology slices are mapped onto corresponding image slices by a registration algorithm. In this regard, ground truth for the tumor regions may be obtained on the structural image slice, such that sub-regions can be associated with the functional data.

At this time, cancerous/malignant regions and benign regions of interest in the images of the training set are known. Then a set of feature vectors to describe different regions of interest may be extracted by image processing algorithms. The feature vectors may include, without limitation, statistical features, gradient features and Gabor filtering features. Different features are extracted to describe the regions of interest in the images. Those features may be collected to discriminate malignant cases between benign cases.

The features with the most discriminant power may be selected through a feature selection algorithm. The discriminant power ensures that the tumor cases can be easily and accurately identified in presence of normal variability within the benign cases. In any case, each region of interest with known class label is digitized by a feature vector. They are used as training samples to train a classifier. The best parameters associated with a classifier are determined through the training procedure.

In one arrangement, the classifier training procedure can train a system/machine based on the urologists' prior knowledge and known ground truth, so the trained system/machine can be used to classify and confirm a new unknown region in the system. One classification method applied aims at minimizing the bound on the generalization error (i.e., error made by the learning machine on data unseen during training) rather than minimizing the training error over the data set.

BRIEF DESCRIPTION OF THE DRAWINGS

The systems and methods may take form in various components and arrangements of components and in various steps and arrangements of steps. The drawings are only for the purpose of illustrating preferred embodiments and are not to be construed as limiting the invention.

DETAILED DESCRIPTION OF THE INVENTION

Reference will now be made to the accompanying drawings, which assist in illustrating the various pertinent features of the various novel aspects of the present disclosure. Although the invention is described primarily with respect to an ultrasound imaging embodiment, the invention is applicable to a broad range of imaging modalities and biopsy techniques, including MRI, CT, and PET, which are applicable to organs and/or internal body parts of humans and animals. In this regard, the following description is presented for purposes of illustration and description. Furthermore, the description is not intended to limit the invention to the form disclosed herein. Consequently, variations and modifications commensurate with the following teachings, and skill and knowledge of the relevant art, are within the scope of the present invention.

Figure 1:
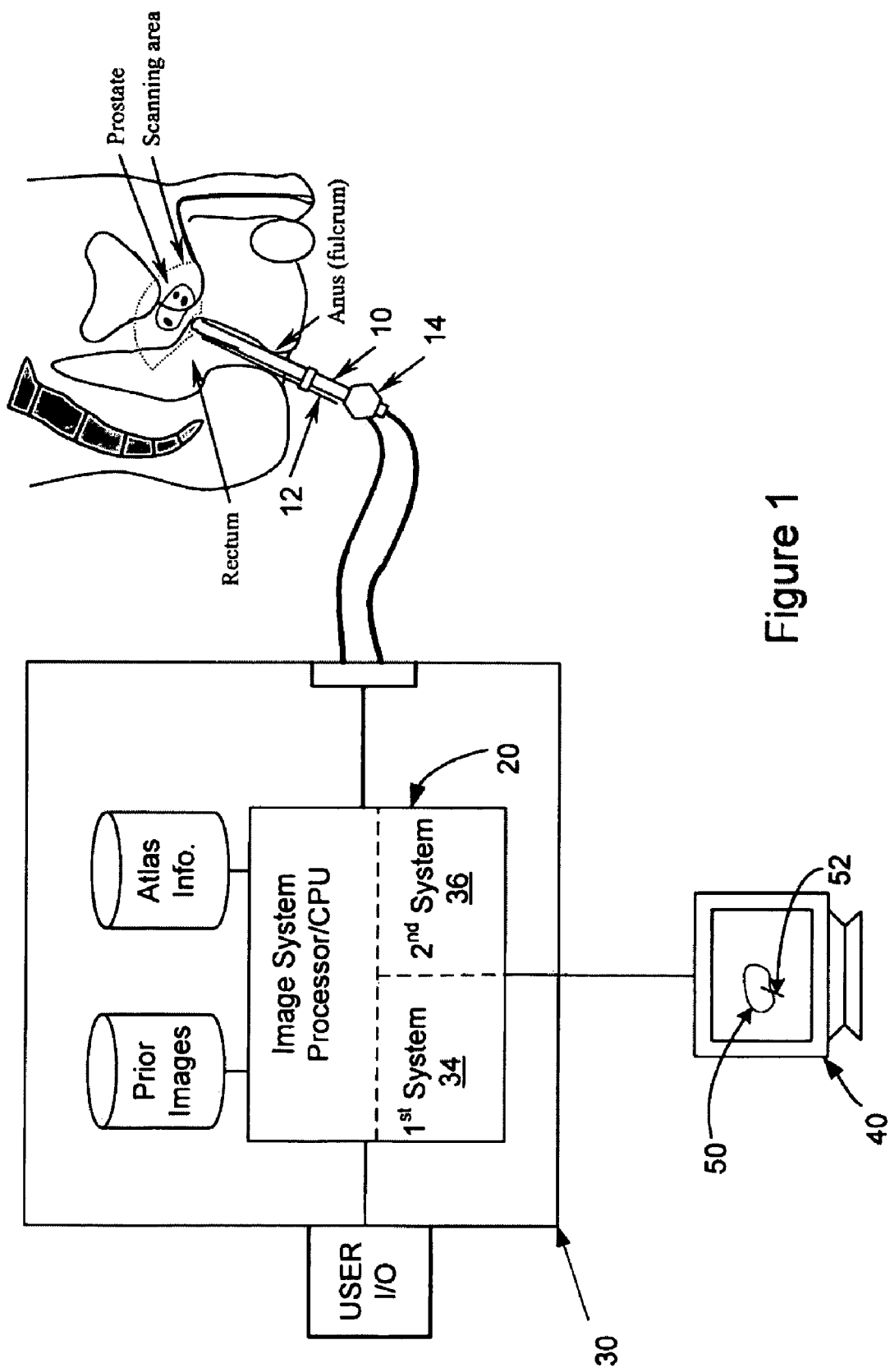
FIG. 1 is a diagrammatic illustration of the transrectal tissue culture procedure.

With reference to FIG. 1, in the illustrated system the tissue culture/biopsy is assisted by an image guidance system 30. The image guidance system 30 provides confirmed tissue culture locations so the urologists can perform tissue culture extraction in these locations. The image guidance system 30 utilizes initial biopsy targeting information provided by a first knowledge-based system 34, where targeting information is confirmed by a second knowledge-based or learning based system 36. Generally, the first system 34 is operative to identify suspicious regions and the second knowledge-based system 36 is used to confirm that the suspicious regions are actually of interest. Further, the system may allow for validating that the extracted tissue is in correct region, location and position.

Initially, an exemplary embodiment of the invention will be described in relation to performing prostate biopsy using transrectal ultrasound (TRUS) guidance. As shown in FIG. 1, an ultrasound probe 10 has a biopsy needle assembly 12 attached to its shaft inserted into the rectum from the patient's anus. The illustrated probe 10 is an end-fire transducer that has a scanning area of a fan shape emanating from the front end of the probe (shown as a dotted outline). The probe handle is held by a robotic arm (not shown) that has a set of position sensors 14. These position sensors 14 are connected to the computer 20 of the imaging system 30 via an analog to digital converter. Hence, the computer 20 has real-time information of the location and orientation of the probe 10 in reference to a unified Cartesian (x, y, z) coordinate system.

With the dimensions of the probe 10 and needle assembly 12 taken into the calculations, the 3D position of the needle tip and its orientation is known. The ultrasound probe 10 sends signal to the image guidance system 30, which may be connected to the same computer (e.g., via a video image grabber) as the output of the position sensors 14. In the present embodiment, this computer is integrated into the imaging system 30. The computer 20 therefore has real-time 2D and/or 3D images of the scanning area in memory 22. The image coordinate system and the robotic arm coordinate system are unified by a transformation. Using the acquired 2D images, a prostate surface 50 (e.g., 3D model of the organ) and biopsy needle 52 are simulated and displayed on a display screen 40 with their coordinates displayed in real-time. A biopsy needle may also be modeled on the display, which has a coordinate system so the doctor has the knowledge of the exact locations of the needle and the prostate.

The computer system runs application software and computer programs which can be used to control the system components, provide user interface, and provide the features of the imaging system. The software may be originally provided on computer-readable media, such as compact disks (CDs), magnetic tape, or other mass storage medium. Alternatively, the software may be downloaded from electronic links such as a host or vendor website. The software is installed onto the computer system hard drive and/or electronic memory, and is accessed and controlled by the computer's operating system. Software updates are also electronically available on mass storage media or downloadable from the host or vendor website. The software, as provided on the computer-readable media or downloaded from electronic links, represents a computer program product usable with a programmable computer processor having computer-readable program code embodied therein. The software contains one or more programming modules, subroutines, computer links, and compilations of executable code, which perform the functions of the imaging system. The user interacts with the software via keyboard, mouse, voice recognition, and other user-interface devices (e.g., user I/O devices) connected to the computer system.

First Knowledge-Based System.

In the present embodiment, the first knowledge-based system 34 is a statistical atlas that identifies areas or regions of interest (ROIs) on a prostate of a patient. In this regard a shape model including statistical information may be generated that may subsequently be fit to a patient prostate image. Such a process is set forth in FIG. 2 and is more fully set forth in co-pending U.S. patent application Ser. No. 11/740,807 entitled "IMPROVED SYSTEM AND METHOD FOR 3-D BIOPSY," having a filing date of Apr. 26, 2006, the entire contents of which are incorporated herein by reference.

Figure 2:
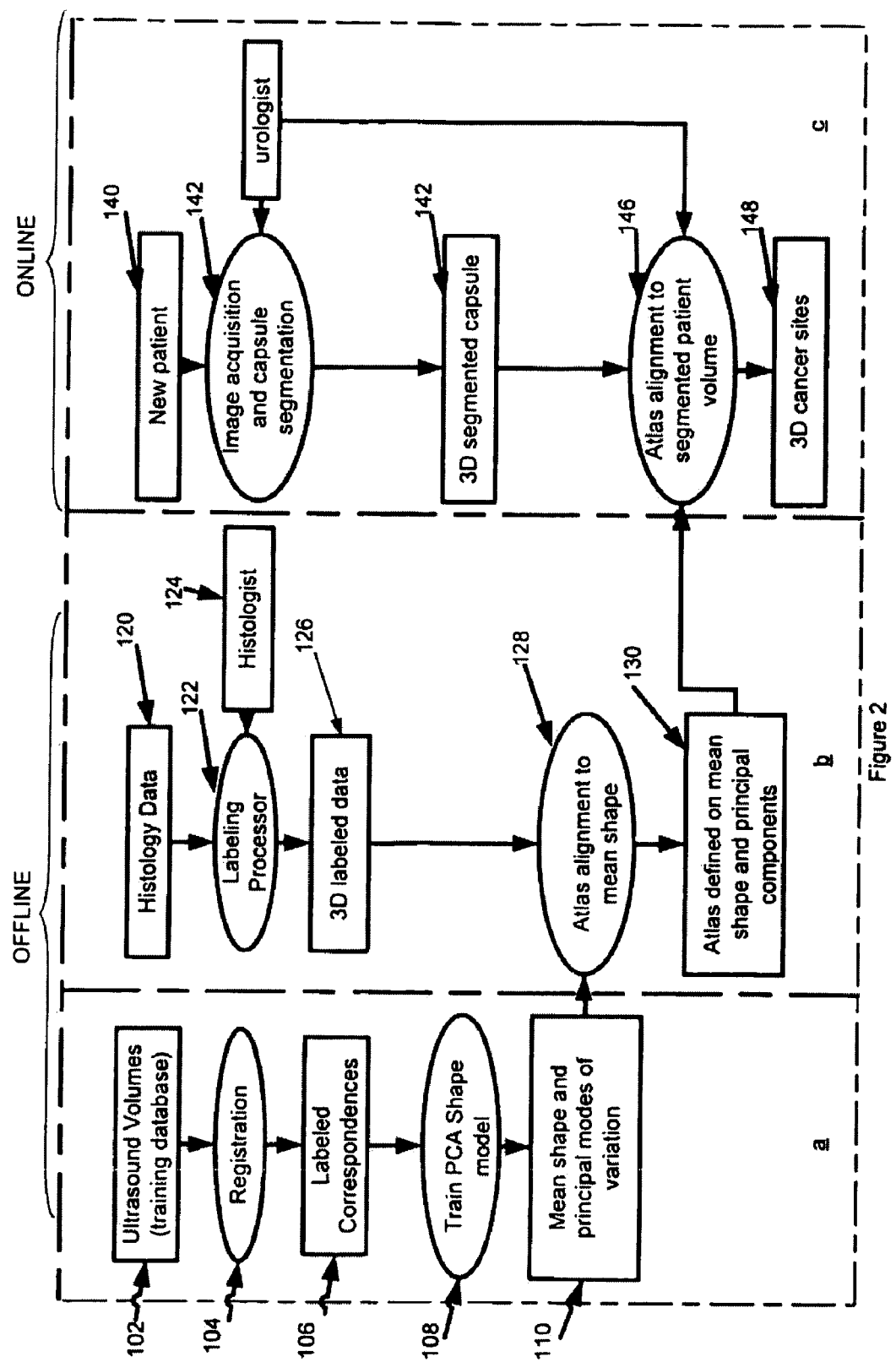
FIG. 2 is the schematic view of the first knowledge-based system.

As shown in the offline portion of FIG. 2, initially, 3-D ultrasound images of multiple prostates are acquired 102 using, for example a TransRectal UltraSound (TRUS) system. The acquired images may then be converted to 3-D orthogonal voxel data (e.g., ultrasound volumes) having equal resolution in all three dimensions. Each of these 3-D individual images may then be represented as a set of two-dimension images. As will be appreciated, such a procedure may be performed on a plurality of patients to obtain a database of ultrasound volumes, which may be utilized to, generate a shape model.

Referring again to FIG. 2, once the ultrasound volumes are obtained 102, compiled and segmented, either manually or using a segmentation program, the ultrasound volumes may be utilized to train a shape model. However, prior to training the shape model, the segmented surfaces must be labeled. That is, corresponding structures within each segmented surface must be labeled to a common reference frame. This is referred to as a registration process 104. See FIG. 2. In this regard, each of the ultrasound volumes are marked by an expert (e.g., histologist) in feature rich regions or regions that distinguish the shape of the surface. The marked points are called landmarks, and they are correspondingly marked in all of the images of the training data/ultrasound volume database.

A process for training the shape model is performed 108. As will be appreciated, the training images reflect a variety of different geometrical prostate shapes. These different shapes must be taken into account in training the system. To this end, an average shape is created from the training images in the form of a mean shape vector 110. Generally, creating the average prostate shape involves labeling a set of feature points corresponding to prostate features/landmarks depicted in each training image in the training set of ultrasound volumes. The locations of the labeled feature points from a training images are used to form vector shapes 108. The average of all the vector shapes 108 is then computed to produce a mean vector shape 110 that represents the average prostate shape. More specifically, a top percentage of Eigen Vectors are selected that account for more than 95% variance of the entire set of images. Accordingly, the projections on the selected Eigen Vectors can then be utilized to align the shape model (e.g., mean shape) to any other shape.

That is, a mean shape and its principal mode of variation are defined 110. These modes of variation can be utilized to fit the mean prostate shape to a prostate image acquired from a patient. Registration of the model to any shape resembling the training shape now becomes a straightforward mathematical process. The projection can be either directly optimized to maximize the similarity between the given shape and the model or the model can be allowed to "warp" freely and may be constrained by requirements of the model that would prevent the model from warping into shapes that do not resembles a prostate.

Statistical Information Collection.

Statistical information collection entails the collection of histology data 120, which are outlined and labeled 122. See FIG. 2. In this regard, prostate cancer locations are identified and mapped for a large group of patient data. These samples are collected and used to compile statistics on the presence of cancer locations. Reference to the database of images whose cancer characteristics are fully known is referred to as ground truth data. This ground truth data may be utilized to generate a look-up-table or LUT/map/atlas that indicates the probability of various regions of developing cancer. These ground truths images may be generated from histological data including histological, slices from actual prostates and/or histological data identified from individual prostate images. The ground truth images are all mapped to a common anatomical frame 126 and contain labels that mark every location of the prostate, i.e. whether cancer is present or not. Such labels may be selected by a histologist 124. Cancer probability maps/atlases are then computed from this data. These maps/atlases can be used for biopsy guidance.

Data from separate prostates is labeled to a common reference frame 126 such that the data may be incorporated into a map/atlas that may be utilized to identify areas within a prostate for a given patient. Such labeling may include selecting a volume as a common volume of reference for a set of image volumes. Each of the remaining volumes may be registered to the chosen common volume of reference so as to create an atlas 128. Then, special coordinates of cancer in each of the remaining image volumes are mapped onto the atlas coordinates in the atlas by transformation that registers the corresponding image volume to the atlas.

In this regard, prostate regions that contain cancer may be identified. For instance, if a plurality of the histological samples of different prostates include cancer in a common area, a region of interest of that region may be identified. The ROI may be a area that may represent an optimal target region for biopsy to identify cancer within that region of the prostate. In any case, once the histological data is labeled into a common 3D reference frame 126, a map/atlas may be aligned 128 with the mean shape of the shape model discussed above. That is, statistical information of the map/atlas (e.g., regions of increased probability of cancer) may be incorporated into the shape model. This shape model and corresponding statistical information 130 may then be fit to an image of a prostate of a patient in an online procedure. Accordingly, statistical information associated with the regions having a high incidence of cancer may be overlaid onto and/or into the image of the prostate of the patient. Accordingly, these regions may be targeted for biopsy.

Fitting the Shape Model to Patient Image

As illustrated in FIG. 2, the online portion involves acquiring a current image 140 for a patient. Once the ultrasound image is acquired it may be segmented 142 to identify the surface of the 3-D volume/capsule 144 and/or the boundaries of individual images (e.g., 2-D or 3-D images). Such segmentation may be performed in any known manner. One such segmentation method is provided in co-pending U.S. patent application Ser. No. 11/615,596, entitled "Object Recognition System for Medical Imaging" filed on Dec. 22, 2006, the contents of which are incorporated by reference herein. The segmented image is then provided for combination with the shape model 146 in order to align the map/atlas information with the acquired image. Biopsy locations may then be identified 148.

Figure 3A:
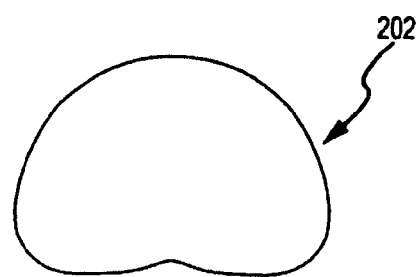
FIGS. 3A-3D illustrate application of the first knowledge based system to a prostate image to define regions of interest.
Figure 3C:
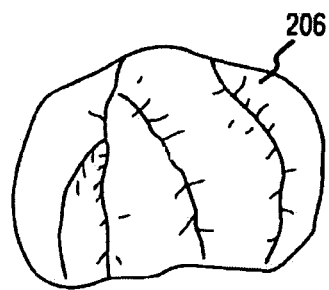
Figure 3B:
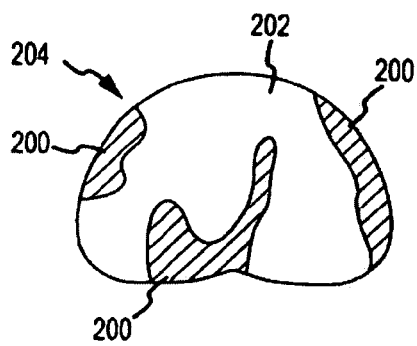
Figure 3D:
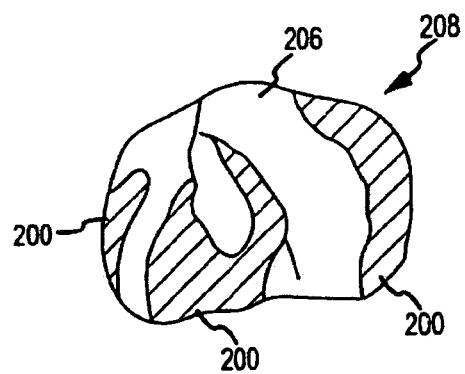

FIGS. 3A-3D graphically illustrate the overall process. Though illustrated as 2D figures, it will be appreciated that the shape model, prostate image and statistical regions (e.g., ROI's) discussed herein may be three dimensional. Accordingly, the statistical information may be displayed on and/or within the prostate image. Initially, the shape model 202 is provided. See FIG. 3A. Statistical information 200 (e.g., ground truth data) corresponding to a current patient (e.g., based on demographics, PSA, etc) is aligned with the shape model 202 so that a completely defined geometrical deformations shape model 204 including statistical information is provided. See FIG. 3B. The deformation shape model 204 may be based on a set of Eigen vectors that allow the model 204 to only be fitted in ways allowed by predetermined limitations of the model. The model may then be applied (e.g., fit) to an acquired ultrasound prostate image 206. See FIG. 3C. The result of this fitting procedure is also the transfer of statistical information to the prostate image 206 of the patient. That is, the statistical information may be applied to the prostate image 206 of the patient to provide a combined image with statistical data 208. See. FIG. 3D. The combined image 208 may be used to define regions of interest on the prostate of the current patient that have, for example, higher likelihood of cancer. Accordingly, a urologist may target such regions for biopsy.

While such regions may have a higher statistical likelihood of being cancerous, simply sampling each of these suggested biopsy regions may result in unnecessary discomfort for the patient. Accordingly, the present invention utilizes a second knowledge-based system to confirm the desirability of performing biopsy on the suggested region. In the presented embodiment, the second knowledge-based system performs a texture/textural analysis and classification of the suggested biopsy regions to confirm whether a biopsy should be taken from the suggested regions.

Figure 4:
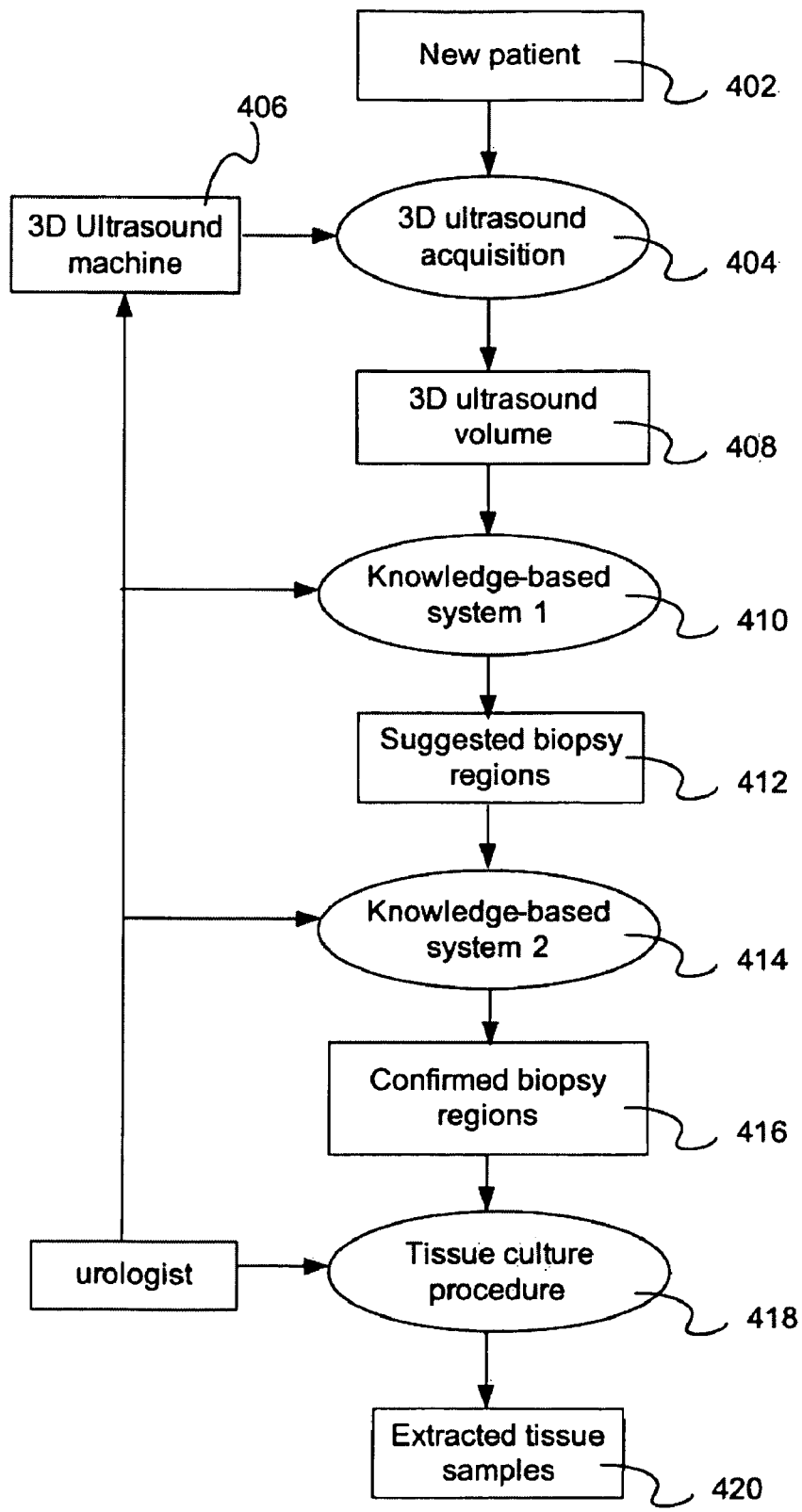
FIG. 4 is an object process diagram of one embodiment of an image guidance system incorporating first and second knowledge-based systems.

With reference to FIG. 4, an overall process 400 utilizing first and second knowledge-based systems to suggest and confirm a tissue extraction/biopsy process is described. For a new patient 402, prostate images are acquired 404 with a 3D ultrasound imaging system 406 to generate a 3-D volume 408. The acquired data 408 is then provided to a first knowledge-based system 410 and fused using a multi-modality image data set or warped using a knowledge-based system such as ATLAS. This first knowledge-based system 410 is a guidance system without any confirmation that provides suggested biopsy regions 412. Then a second knowledge-based system 414 may perform an efficient image textural analysis and classification for those initial suggested biopsy regions. The confirmed regions confirmed 416 (for biopsy) by the second knowledge-based system can provide urologists improved guidance for a biopsy procedure 418 where tissue samples are extracted 420.

Figure 5:
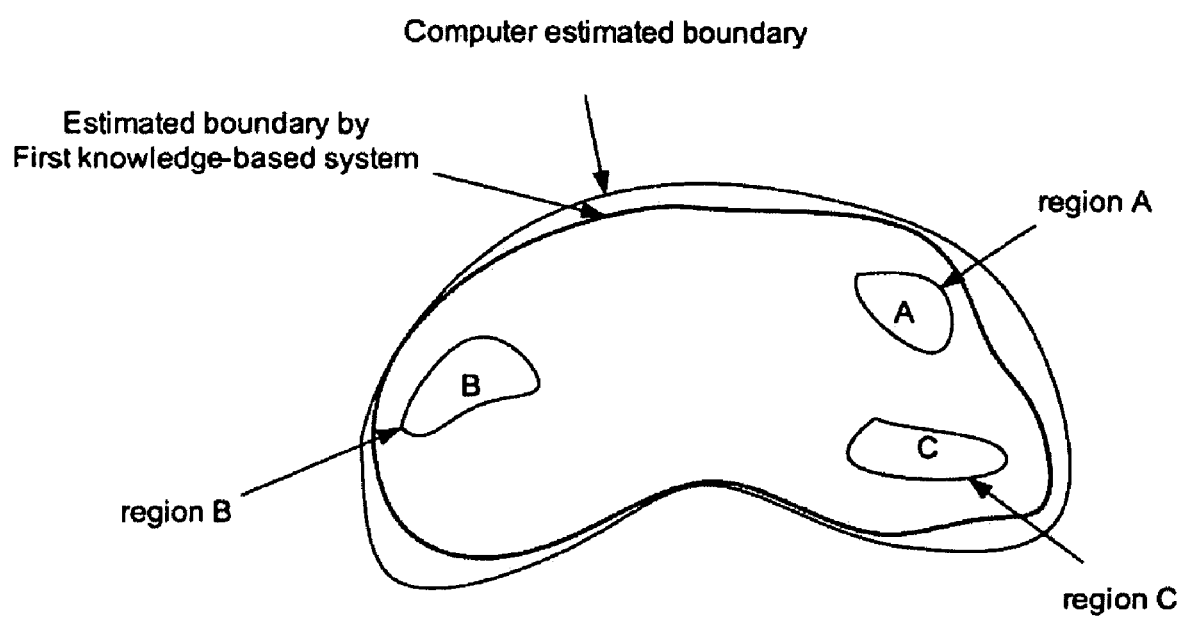
FIG. 5 illustrates application of regions of interest to a prostate image by the first knowledge-based system.

With reference to FIGS. 2 and 5, several high probability suspicious regions A-C where biopsy is suggested are marked out in a prostate image with the help of the first knowledge-based system. As noted above, first a statistical atlas of the spatial distribution of prostate cancer is constructed from histological images of a patient database. Secondly, a probabilistic optimization framework is employed to optimize the biopsy strategy; finally, the optimized biopsy strategy generated in the atlas is mapped to a new patient's image. Accordingly, suggested biopsy regions A-C can be marked out.

Figure 6:
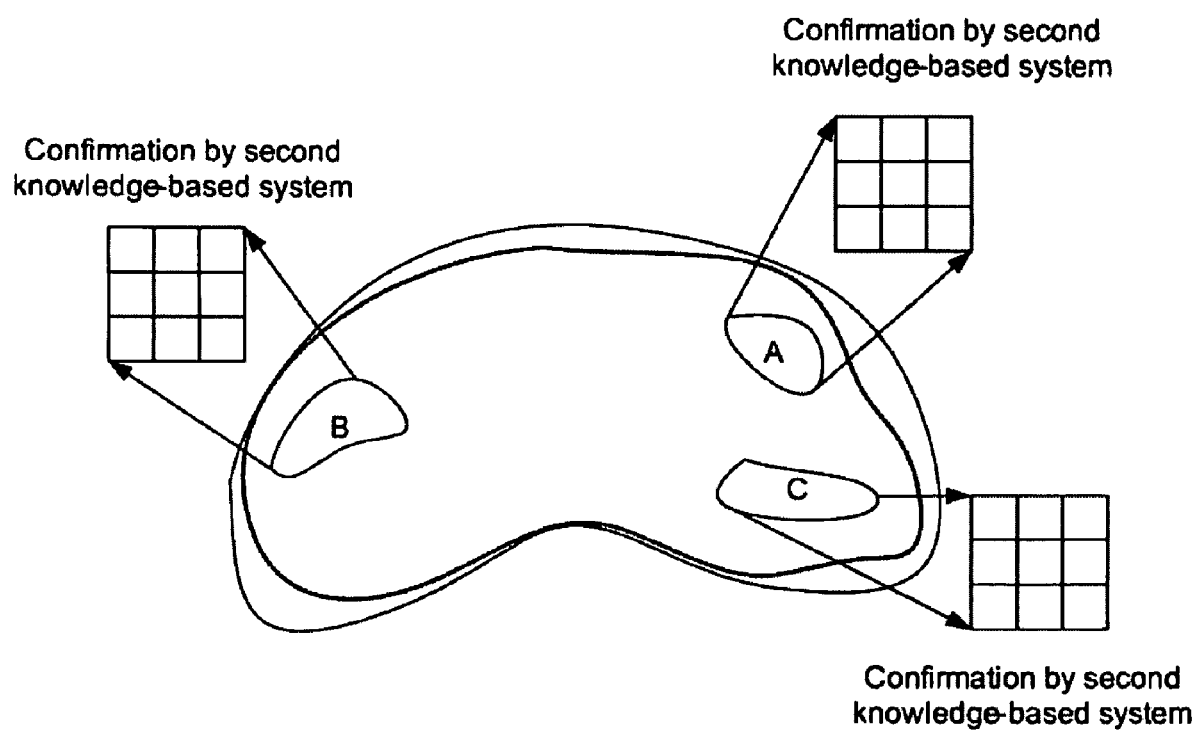
FIG. 6 illustrates analysis of regions of interest in the prostate image of FIG. 5 by the second knowledge-based system.

FIG. 6 illustrated one embodiment of the second knowledge-based system. The suggested biopsy regions A-C provided by the first knowledge-based system are analyzed by the second knowledge-based system, which provides a confirmation whether those regions are likely cancerous or not. Such analysis may be limited to the regions of interest to limit the computational requirements of the system. Further, such analysis may be performed on a pixel by pixel basis, though this is not a requirement.

Figure 7:
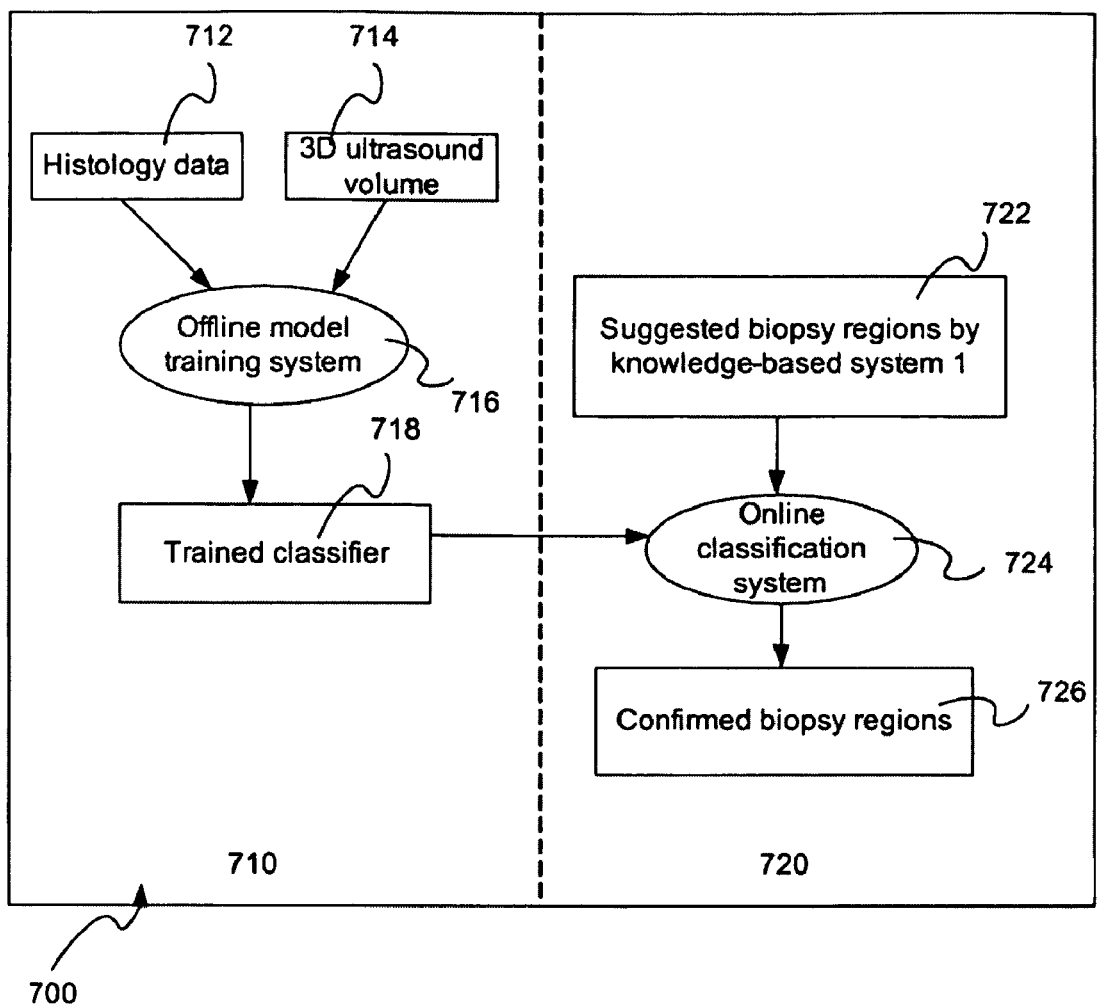
FIG. 7 is an object process diagram of the second knowledge-based system.

With reference to FIG. 7, a process 700 of the second knowledge-based system is described. In the offline model training system 710, inputs to the system include histology data 712 and 3D ultrasound prostate images 714. The histology data and the ultrasound images in the patient database are used 716 to generate tumor ground truth information and train a classifier 718. Then in the online classification 710, the suggested biopsy regions 722 provided by the first knowledge-based system in a new patient's ultrasound image are classified 724 and confirmed 726.

Offline Model Training

Figure 8:
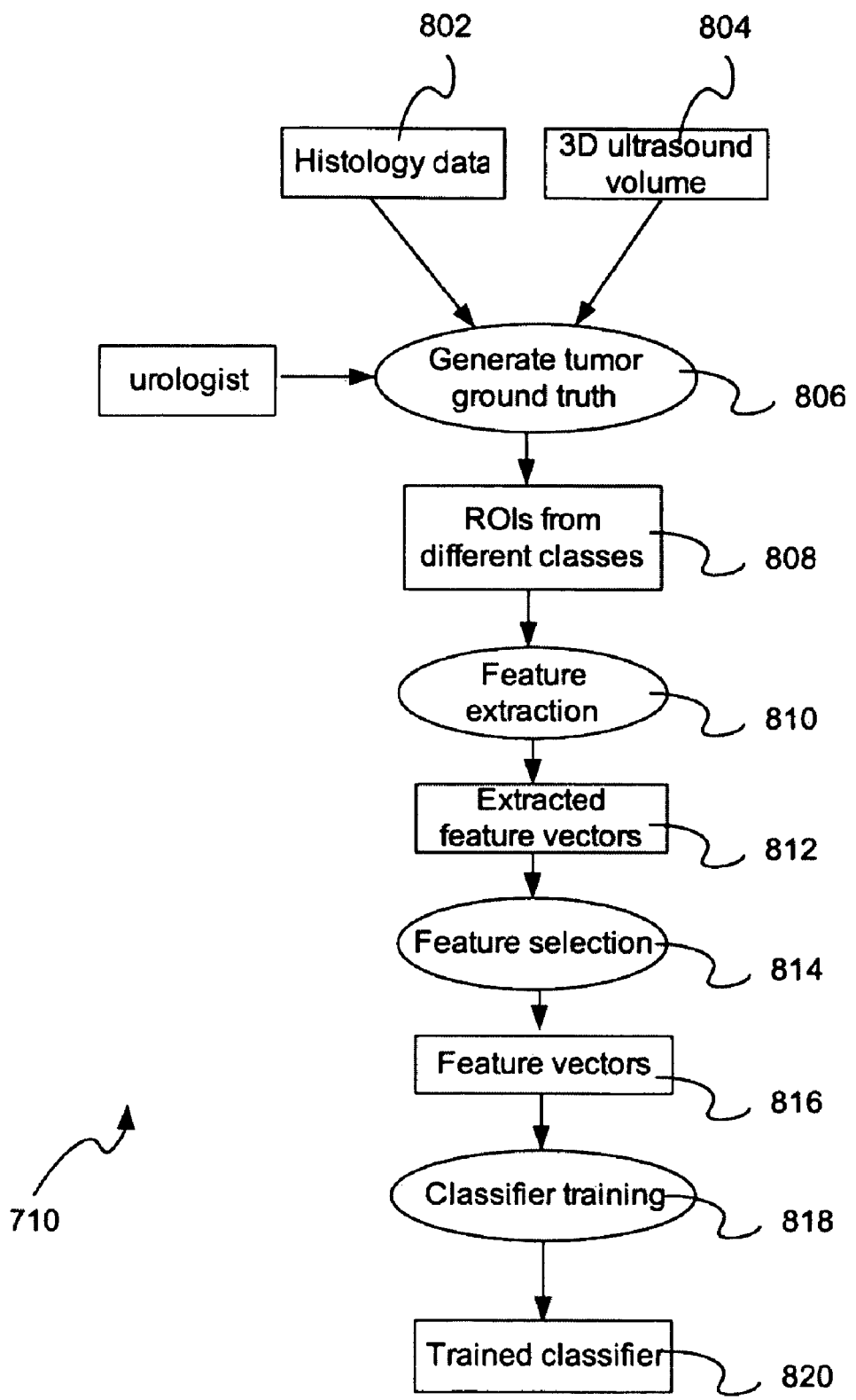
FIG. 8 is an offline model training system for the second knowledge-based system.

FIG. 8 shows the offline model training system 710 for the second knowledge-based system where histology data 802 and 3D ultrasound images 804 are used to generate tumor ground truth information 806. Once ground truth tumor information is generated, regions of interest (ROIs) 808 from different classes of the ground truth tumor information may be identified. A feature extraction process 810 is performed on each different class to generate extracted feature vectors 812. That is, cancerous region and benign region in the training images are known. The features to describe different ROIs are extracted. The feature sets can be written as $F=(f_1, f_2, \ldots, f_N)$, where each $f_n$, $n=1, 2, \ldots, N$ represents each image feature. Also, the best feature sets are, selected through feature selection procedure 814. Then the feature vectors 816 from each ROI are used as inputs in a classifier training process 818 to produce trained classifiers 820 that the second knowledge-based system may utilize to confirm or eliminate suspect regions identified by the first knowledge-based system.

Figure 9:
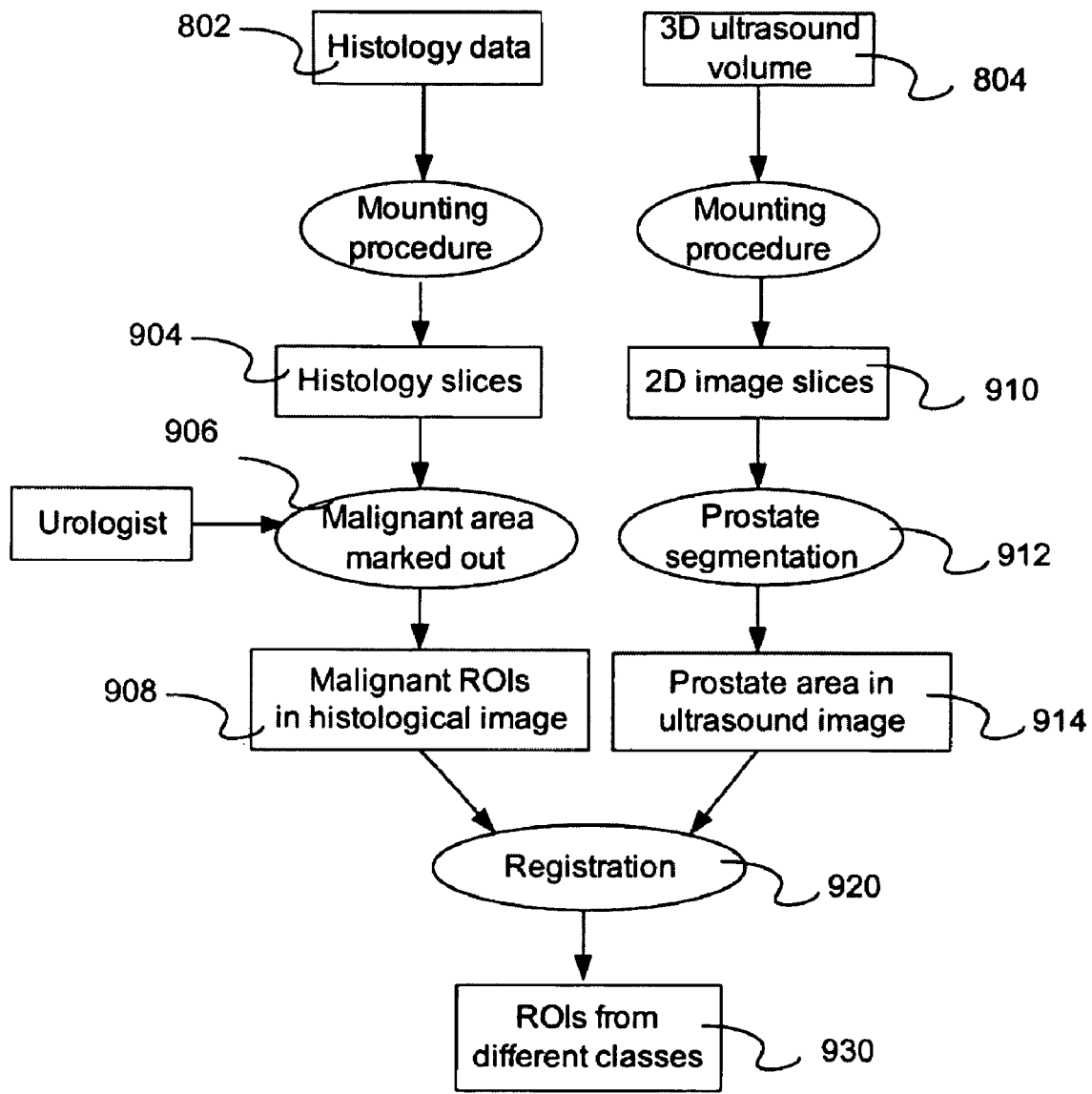
FIG. 9 is a tumor ground truth generation procedure for the second knowledge-based system.

With reference to FIG. 9, the details of generating tumor ground truth information 806 are described. The process is based on a training database including histology data 802 and prostate ultrasound images 804. The overall scheme for the presented utility can be summarized as follows: initially, in the training dataset, the 3D volumes 804 are mounted into 2D image slices 910. The prostate boundary in each 2D ultrasound image is segmented 912 by a semi-automatic or automatic segmentation algorithm. The histology data 802 is also mounted to 2D sliced 904 with tumor regions marked out 906 by urologists are used as references, assisting by a registration procedure 920, the corresponding regions in the prostate ultrasound images can be found. After this step, the cancerous regions and benign regions (ROIs) in the training images are known. Then a set of feature vectors to describe different ROIs is extracted by image processing algorithms. The feature vectors include statistical features, gradient features and Gabor filtering features. The features with the most discriminant power are selected through a feature selection algorithm. As a result, each ROI with known class label is digitized by a feature vector. They are used as training samples to train a classifier. The best parameters associated with a classifier are determined through the training procedure. This is offline model training. For a new patient, the knowledge-based system-1 provides initial suggested biopsy regions (ROIs) in the ultrasound image. The feature vectors are then extracted in each of these ROIs. The trained classifier from offline training can determine if these ROIs are truly cancerous or not. This is online classification procedure. The knowledge-based system-2 works as a confirmation sub-system. So the Urologists can do tissue culture in those confirmed biopsy regions.

For segmentation of the prostate image, accurate boundaries are needed. Semi-automatic or automatically segmentation methods are used to segment prostate boundary in the ultrasound image. This application may use three different methods: In a first method, a genetic algorithm (GA) approach is used. This approach is an extension to a point distribution model (PDM). The PDM is a model of object contour that can be defined with certain number of parameters. The parameter value varies in the certain ranges in which result different shapes of contours. The main advantage of GAs is its adaptive search techniques designed to search for near-optimal solutions of large-scale optimization problems with multiple local maxima. GAs are independent of initialization parameters and can efficiently optimize functions in large search spaces. Composing PDM and GAs can efficiently optimize the search space and adjust the best contour fit to the prostate boundary. By initial data analysis, it was confirmed that the use of PDM and GAs techniques can lead to obtaining prostate contours in the real time.

In a second method, a level set strategy may be used for contour estimation. An automated algorithm is proposed to delineate the boundary of the prostate. This provides a methodology that models the prostate images as combination of homogeneous regions with different gray levels, and minimizes the energy functional based on the regional information of the image. In this algorithm, the urologist puts few initial points near the prostate capsule and computer then automatically estimates the final boundary. The computer algorithm models the prostate images as combination of homogeneous regions with different gray levels, and minimizes the energy functional based on the regional information of the image. This strategy is implemented in a level set framework, where, the contour is represented implicitly in the level set function. A finite difference method embedded in a steepest descent framework is used to compute the stabilized boundary in the narrow band search region. Level set representation of curves or surfaces is particularly useful and necessary for the motion of curves and surfaces. Such a methodology is set forth in U.S. application Ser. No. 11/615,596, entitled "Object Recognition System, for Medical Imaging," having a filing date of Dec. 22, 2006, the contents of which are incorporated herein by reference.

In a third method, gradient vector flow (GVF) snakes are applied to estimate the boundary of the prostate. Its advantages are insensitivity to contour initialization and its ability to deform into highly concave part of the object compared to other deformable contour models. The GVF snakes replace the standard external force in the traditional snakes with a static external force which does not change with time or depend on the position of the snake itself. The new static external force is called gradient vector field. GVF snakes first calculate of a field of forces, called the GVF forces, over the image. The GVF forces are calculated by applying generalized diffusion equations to both components of the gradient of an image edge map. The GVF forces are derived from a diffusion operation, they tend to extend very far away from the object. This extends the "capture range" so that snakes can find objects that are quite far away from the snake's initial position. This same diffusion creates forces which can pull active contours into concave regions. Such a methodology is set forth in co-pending U.S. application Ser. No. 11/833,404, entitled "Improved Object Recognition System for Medical Imaging," having a filing date of Aug. 3, 2007, the entire contents of which are incorporated herein by reference.

Figure 10:
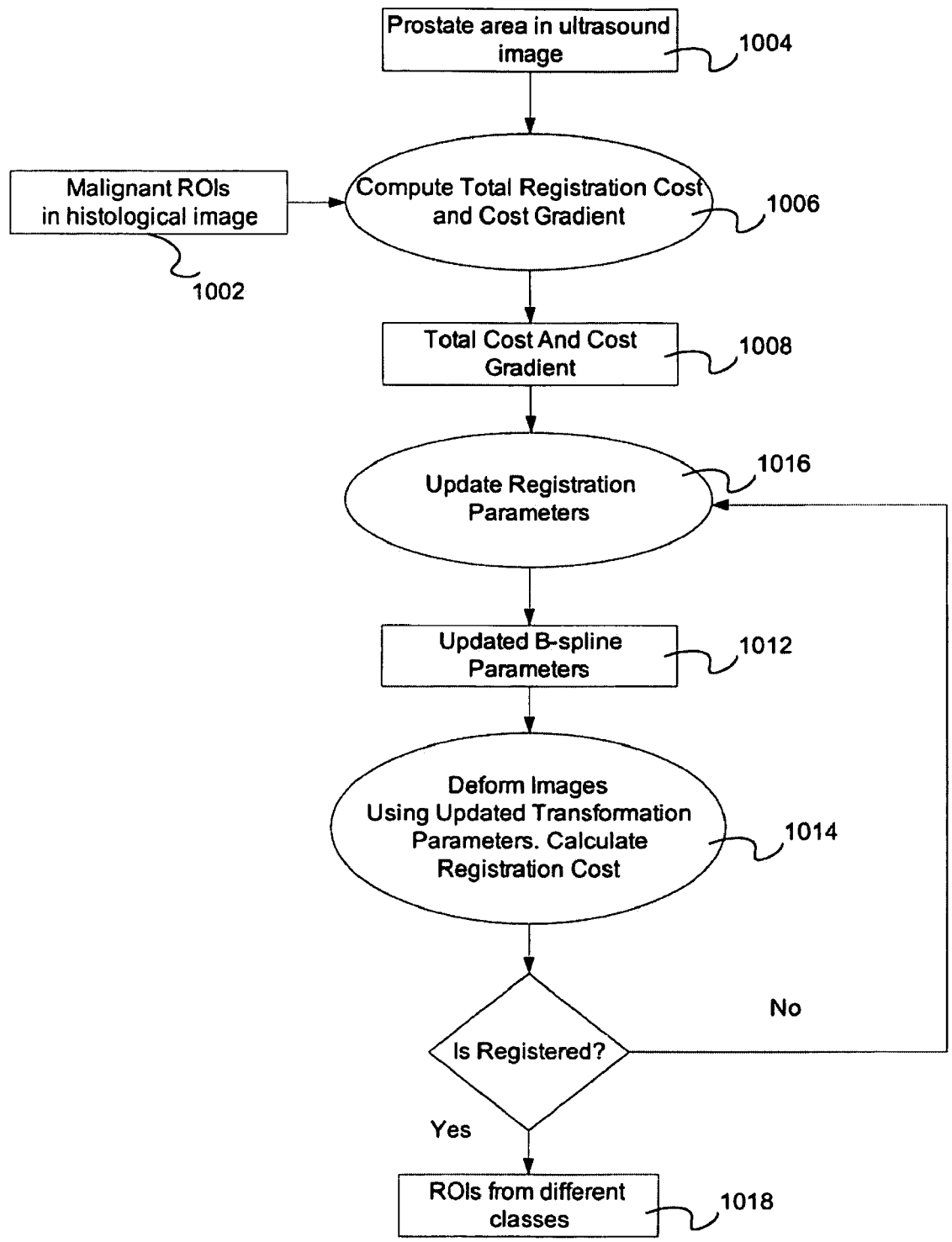
FIG. 10 is a registration procedure for the second knowledge-based system.

As discussed in FIG. 10, that the segmentation results are used for registration. One registration process is set forth in FIG. 10, which shows the registration procedure for the second knowledge-based system. The main goal is to find correspondences between a histological image slice 1002 and a corresponding 2D ultrasound image slice 1004, thus providing ground truth to train a classifier. Image registration establishes a common frame of reference for a meaningful comparison between the two images. Image registration is often posed as an optimization problem which minimizes an objective function representing the difference between two images to be registered. The symmetric squared intensity difference is chosen as the driving function. In addition, regularization constraints may be applied so that the deformation follows a model that matches closely with the deformation of real-world objects. The regularization is applied in the form of bending energy and inverse-consistency cost. Inverse-consistency implies that the correspondence provided by the registration in one direction matches closely with the correspondence in the opposite direction. Most image registration methods are uni-directional and therefore contain correspondence ambiguities originating from choice of direction of registration. In the algorithm proposed here, the forward and reverse correspondences are computed simultaneously and bound together through an inverse consistency cost term. The inverse consistency cost term assigns higher cost to transformations deviating from being inverse-consistent. While inverse consistency minimizes the correspondence ambiguity, it also helps the transformation perform better by forcing it out of local minima. Initially, the cost function for performing image registration over the image is calculated 1006, in which the correspondence is estimated in both directions such that the registration is inverse consistent. Inverse consistency is a desirable property of transformation and ensures that there is no correspondence ambiguity if the direction of registration is reversed.

$$C = \sigma \left( \int_\Omega |I_1(h_{1,2}(x)) - I_2(x)|^2 dx + \int_\Omega |I_2(h_{2,1}(x)) - I_1(x)|^2 dx \right) + \qquad (1)$$
$$\rho \left( \int_\Omega \|L(u_{1,2}(x))\|^2 dx + \int_\Omega \|L(u_{2,1}(x))\|^2 dx \right) +$$
$$\chi \left( \int_\Omega \|h_{1,2}(x) - h_{2,1}^{-1}(x)\|^2 dx + \int_\Omega \|h_{2,1}(x) - h_{1,2}^{-1}(x)\|^2 dx \right)$$

where, $I_1(x)$ and $I_2(x)$ represent the intensity of image at location x, represents the domain of the image. $h_{i,j}(x)=x+u_{i,j}(x)$ represents the transformation from image $I_i$ to image $I_j$ and u(x) represents the displacement field. L is a differential operator and the second term in Eq. (1) represents an energy function. σ, ρ and χ are weights to adjust relative importance of the cost function.

In equation (1), the first term represents the symmetric squared intensity cost function and represents the integration of squared intensity difference between deformed reference image and the target image in both directions. The second term represents the energy regularization cost term and penalizes high derivatives of u(x). As presented, L is represented as a Laplacian operator mathematically given as: $L=\nabla^2$. The last term represents the inverse consistency cost function, which penalizes differences between transformation in one direction and inverse of transformation in opposite direction. The total cost 1008 is computed as a first step in registration.

The optimization problem posed in Eq. (1) is solved in an iterative process by using a B-spline parameterization 1012, such that $$h(x) = x + \sum_i c_i \beta_i(x) \qquad (2)$$

where, $\beta_i(x)$ represents the value of B-spline at location x, originating at index i. In the presented registration method, cubic B-splines are used. A gradient descent scheme is implemented based on the above parameterization. The total gradient cost is recalculated 1014 with respect to the transformation parameters in every iteration. The transformation parameters are updated using the gradient descent update rule. Images are deformed into shape of one another using the updated correspondence and the cost function and gradient costs are calculated until convergence defining ROI's for different classes 1018. The registration is performed hierarchically using, a multi-resolution strategy in both, spatial domain and in domain of basis functions. The registration may be performed at $\frac{1}{4}^{th}$, ½ and full resolution using knot spacing of 8, 16 and 32. In addition to being faster, the multi-resolution strategy helps in improving the registration by matching global structures at lowest resolution and then matching local structures as the resolution is refined.

Figure 11:
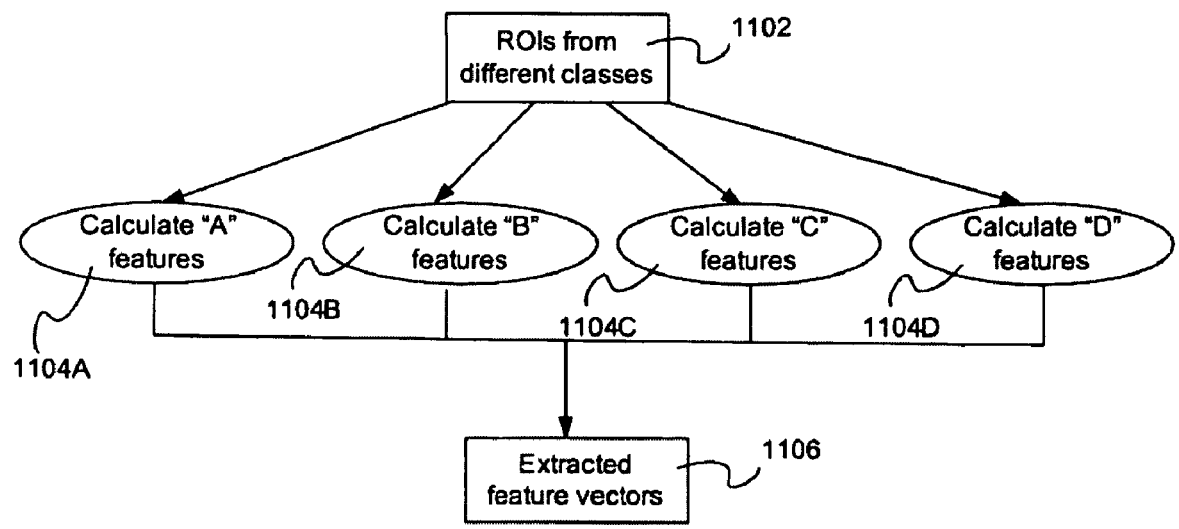
FIG. 11 is a feature extraction procedure for the second knowledge-based system.

After registration feature, extraction 810 is applied to quantitatively describe the region of interests 808 from different classes (cancerous regions and normal regions in ultrasound image). See FIG. 8. This step is the key to the future classifier training since the image regions are now represented by these features. FIG. 11 shows a feature extraction procedure of the offline model training. A set of features 1104A-D are extracted from each ROI 1102. The features chosen here include the following: "A" features: first order statistical features; "B" features: second order statistical features; "C" features: gradient features; "D" features: Gabor bank filter features. A variety of extracted features are specifically suitable to texture analysis of prostate ultrasound image. The plan is to measure features of the region of interest and then use these features to determine class membership including, for instance, whether it is benign or malignant.

Suppose a ROI to be analyzed: C, is rectangular and has $N_x$ rows and $N_y$ columns. See, e.g., FIG. 6. Let $L_x=\{1, 2, \ldots, N_x\}$ be the rows, $L_y=\{1, 2, \ldots, N_y\}$ be the columns. Assuming a pixel u inside this region has coordinates: $(L_x, L_y)$, and intensity $f(u)$, and there are total of N ($N=N_x \times N_y$) pixels in the region.

The first-order texture features include maximum, minimum, mean and standard deviation in a ROI (addresses the statistical distribution of digital gray scale values to compare cancerous and non-cancerous biopsy sites within a gland) are extracted.

$$F_1 = \text{Max}_{u_t \in c}[f(u_t)] \qquad (3)$$

$$F_2 = \text{Min}_{u_t \in c}[f(u_t)] \qquad (4)$$

$$F_3 = \frac{\sum_{n=1}^{N} f(u_n)}{N} \qquad (5)$$

$$F_4 = \sqrt{\frac{1}{N-1} \sum_{n=1}^{N} (f(u_n) - F_3)^2} \qquad (6)$$

Gray level co-occurrence Matrix (GLCM) proposed by R. M. Haralick, K. Shanmugan, and I. Dinstein, "Textural features for image classification," IEEE Trans. Syst. Man, Cybern., Vol. SMC-3, pp. 610-621, 1973, the contents of which are incorporated herein can be used to compute second-order features which have perceptual meaning. It is an indication of how different combinations of gray levels exist in a portion of the image. GLCM is generated from a small square window of the image. Within the window, unordered pairs of pixels are examined that are separated by a given distance and are oriented to each other by a given angle. In general, the window size here are 3×3 and 5×5 pixels, and angles of 0, 45, 90, or 135 are used. An entire image can be analyzed by moving the window across the image in an overlapping manner, advancing one pixel column to the right, then one pixel row downward at a time.

The definition of GLCM's is; as follows: suppose $G_x = \{0, 1, \ldots, N_R - 1\}$ be the set of $N_R$ quantized gray levels. The ROI C can be represented as a function that assigns some gray level in G to each pixel or pair of coordinates in $L_x \times L_y$. The texture-context information is specified by the matrix of relative frequencies $P_{ij}$ with two neighboring pixels separated by distance d occur on the image, one with gray level i and the other with gray level j. Such matrices of gray-level co-occurrence frequencies are a function of the angular relationship and distance between the neighboring pixels.

Let p(i, j) be the (i, j)th entry in a normalized GLCM. The mean and standard deviations for the rows and columns of the matrix are:

$$\mu_x = \sum_i \sum_j i \square p(i, j), \mu_y = \sum_i \sum_j j \square p(i, j)$$

$$\sigma_x = \sum_i \sum_j (i - \mu_x)^2 \square p(i, j), \sigma_y = \sum_i \sum_j (j - \mu_y)^2 \square p(i, j).$$

A set of four features, is constructed from the GLCM which are: contrast, entropy, energy, homogeneity. The features are as follows, Energy: provides the sum of squared elements in the GLCM;

$$F_5 = \sum_i \sum_j p(i, j)^2 \qquad (7)$$

Contrast: measures the local variations in the GLCM;

$$F_6 = \sum_{n=0}^{N_g-1} n^2 \left\{ \sum_{i=1}^{N_x} \sum_{j=1}^{N_y} p(i, j) \bigg| |i, j| = n \right\} \qquad (8)$$

Correlation: measures the joint probability occurrence of the specified pixel pairs;

$$F_7 = \frac{\sum_i \sum_j (ij) p(i, j) - \mu_x \mu_y}{\sigma_x \sigma_y} \qquad (9)$$

Homogeneity: measures the closeness of the distribution of elements in the GLCM to the GLCM diagonal.

$$F_8 = \sum_i \sum_j \frac{1}{1 + (i - j)^2} p(i, j) \qquad (10)$$

Gradient operators are used here to characterize microtextures well. 2D directional gradient and 2D gradient magnitude operators are used to separate faint and not well-defined textural differences between normal and pathological 2D structures in the prostate.

$$F_9 = \sqrt{\left(\frac{\partial}{\partial x} f(u)\right)^2 + \left(\frac{\partial}{\partial y} f(u)\right)^2} \qquad (11)$$

Where $$\frac{\partial}{\partial x} = f(x + 1, y) - f(x, y) \text{ and } \frac{\partial}{\partial y} = f(x, y + 1) - f(x, y).$$

The Gabor filter bank is also used to capture image, features in multi-scales and multi-orientations. The Gabor function is the modulation of a Gaussian with a sinusoid. 2D Gabor filter has been widely used for various pattern recognition problems. The mother function of the two-dimensional Gabor filter is $$g(x, y) = \frac{1}{2\pi \sigma_x \sigma_y} \exp\left[-\frac{1}{2}\left(\frac{x^2}{\sigma_x^2} + \frac{y^2}{\sigma_y^2}\right)\right] \cos(2\pi \phi x) \qquad (12)$$

Where $\phi$ is the frequency of a sinusoidal plan wave along the X-axis.

$$F_{10} = \text{Gabor}(f(u)) \qquad (13)$$

Compared with other existing feature extraction strategies, this strategy allows for extracting a variety of features 1106 specifically suitable to texture analysis of prostate ultrasound image, and a large number of features' combination from different filters ensures capture of a large range of information from the datasets.

After feature extraction, the next step is feature selection 814. See FIG. 8. The goal of feature selection is to choose the best feature set to characterize the property of ROIs. Once a number of features are obtained, the next question is how to select the most important features so as to reduce their number and at the same time retain as much as possible of their class discriminant powers. Feature selection is crucial for machine learning. If some features are with little discriminant power, the subsequent design of a classifier may lead to poor performance. This feature selection is to ensure a large number of features extracted are truly useful to describe the image properties from different classes. In this application, a method is applied which called mutual information feature selection (MIFS). See R. Battiti, "Using mutual information for selecting features in supervised neural net learning," IEEE Trans. Neural Networks, Vol. 5, pp. 537-550, 1994, which is incorporated by reference herein.

MIFS is a powerful tool for feature selection compared with other existing methods for the following reasons: (1) MIFS not only evaluates the information content of each feature with respect to the output class, but also with respect to each of the other features; (2) the traditional feature selection for classification is classifier-dependent. In contrast, MIFS is a classifier-independent technique. That means, the best feature subset is chosen regardless of the chosen classifier.

MIFS can be explained as follows: denote X as a random variable, describing a texture feature and C is a random variable, describing the class. Then the mutual information I(C; X) is a measure of the amount of information that feature X contains about the class C. Thus mutual information provides a criterion for measuring the effectiveness of a feature for the separation of the two classes. Interdependence between feature values and classes is proportional to the value of I(C; X) and the interdependence among the features is, denoted by I($X_1$; $X_2$) that should be minimized to avoid selecting two or more similar features. Therefore, the objective is to maximize I(C; X) and minimize I($X_1$; $X_2$). The mutual information between the feature values and classes can be calculated as follows:

$$I(C;X) = H(C) - H(C|X), \qquad (14)$$

Where the entropy H(C) measures the degree of uncertainty entailed by the classes, the conditional entropy H(C|X) measures the degree of uncertainty entailed by the set of classes C given the set of feature values X. The entropy H(C) depends mainly on classes. The mutual information, I(C; X), is maximum when the class is totally dependant on the feature, while it is minimum when the class and the feature are totally independent. The mutual information among different features I($X_1$; $X_2$) is calculated as follows:

$$I(X_1;X_2) = H(X_2) - H(X_2 - X_1) \qquad (15)$$

The MIFS algorithm is used here to select features from the combined set of features.

As discussed in FIG. 8, after feature selection, classifier training is performed offline. Letting vector x∈R$^n$ denote a feature vector to be classified (here the feature vector is obtained after feature extraction and selection), and letting scalar d denote its class label (i.e. d∈{±1}). In addition, let {($x_i$,$d_i$), i=1, 2, . . . , N} denote a given set of N training examples, where each sample $x_i$ has a known class label $d_i$. The problem then becomes how to determine a classifier ƒ(x) (i.e., a decision function) that can correctly classify an input pattern (not necessarily from the training set). This application, uses two methods for classification.

In a first method, neural networks (NN) are used as classifiers. An NN is an information-processing system that is based on generalization of human cognition or neural biology. It is composed of many artificial neurons that are linked together according to a specific network architecture. The objective of the neural network is to transform the inputs into meaningful outputs. A typical neural network has three layers: input layer, hidden layer and output layer, which are interconnected by modifiable weights, represented by links between layers. Neural networks can be considered as nonlinear function approximating tools (i.e., linear combinations of nonlinear basis functions), where the parameters of the networks should be found by applying optimization methods. In general it is enough to have a single hidden layer neural network to learn the approximation of a nonlinear function. A method based on gradient descent is used in the error-back propagation algorithm for training such multilayer networks. It is a powerful method for classification and has been applied widely in other areas for computer aided diagnosis.

In a second method, support vector machines (SVM) are used. Compared with all traditional classification methods, SVM is a constructive learning procedure rooted in statistical learning theory. It is based on the principle of structural risk minimization, which aims at minimizing the bound on the generalization error (i.e., error made by the learning machine on data unseen during training) rather than minimizing the mean square error over the data set. As a result, an SVM tends to perform well when applied to data outside the training set. It has been demonstrated that it can outperform many other existing methods in many applications. Here SVM is applied to classify the cancerous regions and non-cancerous regions in prostate ultrasound images.

For classification, a (nonlinear) SVM classifier in concept first maps the input data vector x into a higher dimensional space H through an underlying nonlinear mapping $\Phi(x)$, then applies linear classification in this mapped space. That is, an SVM classification function can be written in the following form:

$$f_{SVM}(x) = w^T \Phi(x) + b \tag{16}$$

where parameters w, b are determined from the training data samples. This is accomplished through minimization of the following so-called structural risk function:

$$J(w, \xi) = \frac{1}{2} w^T w + C \sum_{i=1}^{N} \xi_i, \tag{17}$$

subject to $d_i f_{SVM}(x_i) \geq 1 - \xi_i$, $\xi_i \geq 0$; $i=1, 2, \ldots, N$, where C is a user-specified, positive parameter, $\xi_i$ are slack variables. In particular, when the two classes are separable, minimizing the structural risk in (17) amounts to maximizing the separating margin between the two classes.

The cost function in (17) constitutes a balance between the empirical risk (i.e., the training errors reflected by the second term) and model complexity (the first term). The parameter C controls this trade-off. The purpose of using model complexity to constrain the optimization of empirical risk is to avoid over fitting, a situation in which the decision boundary too precisely corresponds to the training data, and thereby fails to perform well on data outside the training set.

A training sample $(x_i, d_i)$ is called a support vector when $d_i f_{SVM}(x_i) \leq 1$. Introducing a so-called kernel function K(x, y) ≡ $\Phi(x)^T \Phi(y)$, the SVM function $f_{SVM}(x)$ can be rewritten in (16) in a kernel form as follows $$f_{SVM}(x) = \sum_{i=1}^{N_s} \alpha_i K(x, s_i) + b, \tag{18}$$

where $s_i$, $i=1, 2, \ldots, N_s$, denote the support vectors. In general, support vectors constitute only a small fraction of the training samples $\{x_i, i=1, 2, \ldots, N\}$.

From (18), the decision function can be directly rewritten through the kernel function K(.,.) without the need to specifically addressing the underlying mapping $\Phi(.)$. In this embodiment, two kernel types are considered: polynomial kernels and Gaussian radial basis functions (RBF). These are among the most commonly used kernels in SVM research, and are known to satisfy Mercer's condition. They are defined as follows:

1. Polynomial kernel:

$$K(x,y) = (x^T y + 1)^p \tag{19}$$

where p>0 is a constant that defines as the kernel order.

2. RBF kernel:

$$K(x, y) = \exp\left(-\frac{\|x - y\|^2}{2\sigma^2}\right) \tag{20}$$

where $\sigma > 0$ is a constant that defines the kernel width.

In the present application, a 10-fold cross validation procedure is applied during training to choose the right parameters for the two classifiers. In the 10-fold cross validation, first, all the data is randomly divided into 10 equal-sized subsets. Second, the classifier model is trained 10 times; during each time one of the 10 subsets is held out in turn while the remaining 9 subsets are used to train the classifier; the trained classifier is then used to classify the held-out subset, and the classification result is recorded. In the end, the classification results for the 10 subsets are averaged to obtain an estimate of the generalization error of the classifier model.

Figure 12:
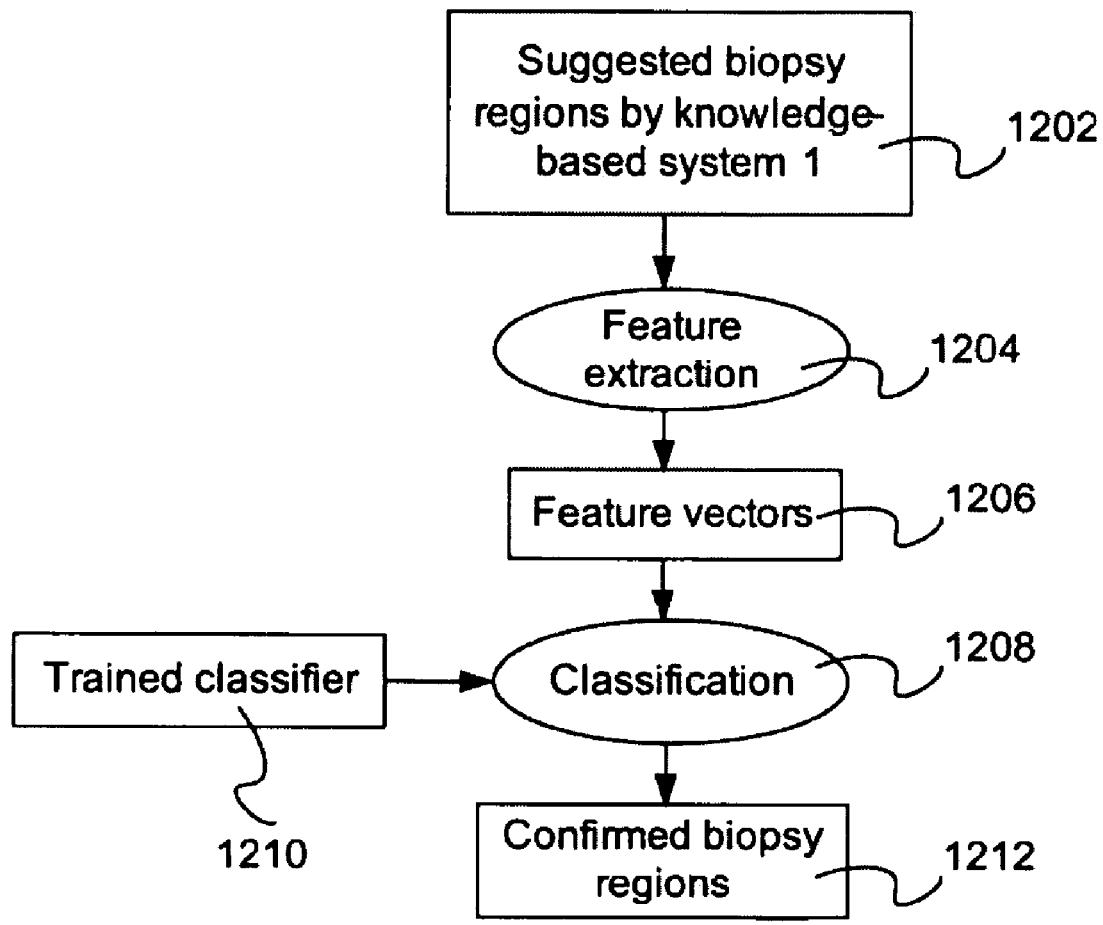
FIG. 12 is an online classification system for the second knowledge-based system.
Figure 13:
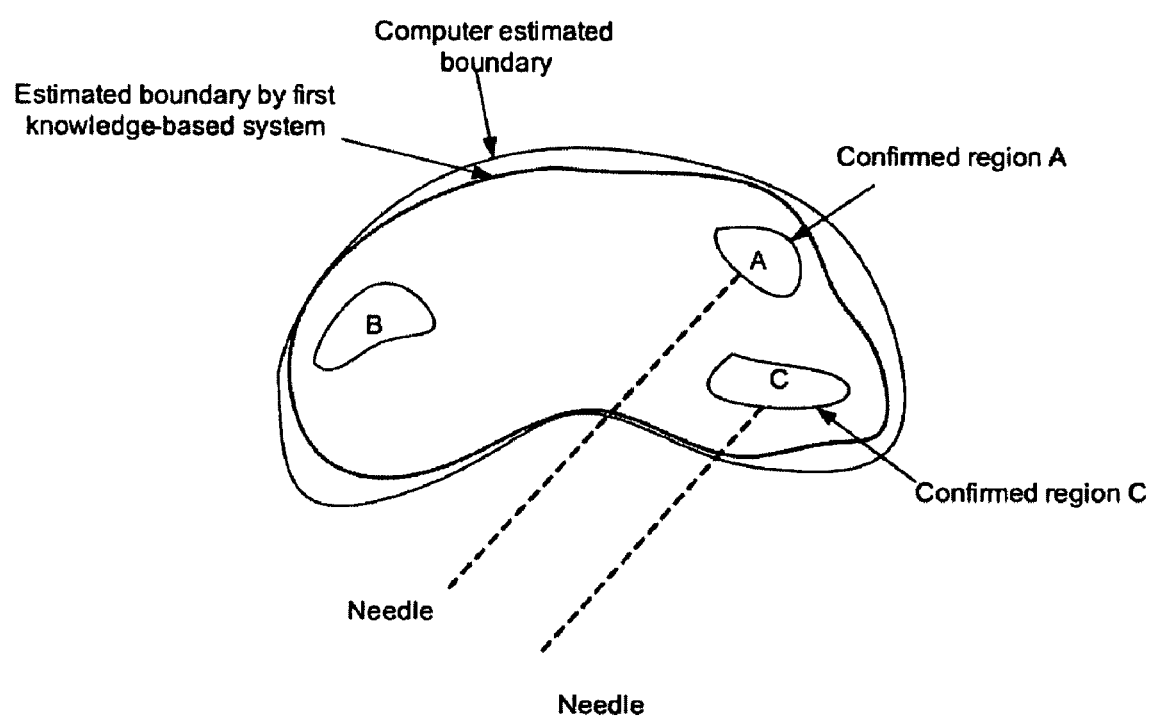
FIG. 13 illustrates confirmed regions of interest on a prostate image.

With reference to FIGS. 12 and 13, the online classification system for the second knowledge-based system is described. For a new patient, the suggested biopsy regions A-C in an ultrasound image are obtained 1202 from the first knowledge-based system, then the same features selected from offline model training procedure are extracted 1204 from those ROIs. The extracted feature vectors 1206 are then fed into a classification process 1208 with the trained classifiers 1210 to decide whether the region is cancerous or not. This is a confirmation procedure 1212; afterwards, the confirmed biopsy regions (e.g., regions A and C in FIG. 13) are obtained and can give urologists a better guidance to do biopsy.

Figure 14:
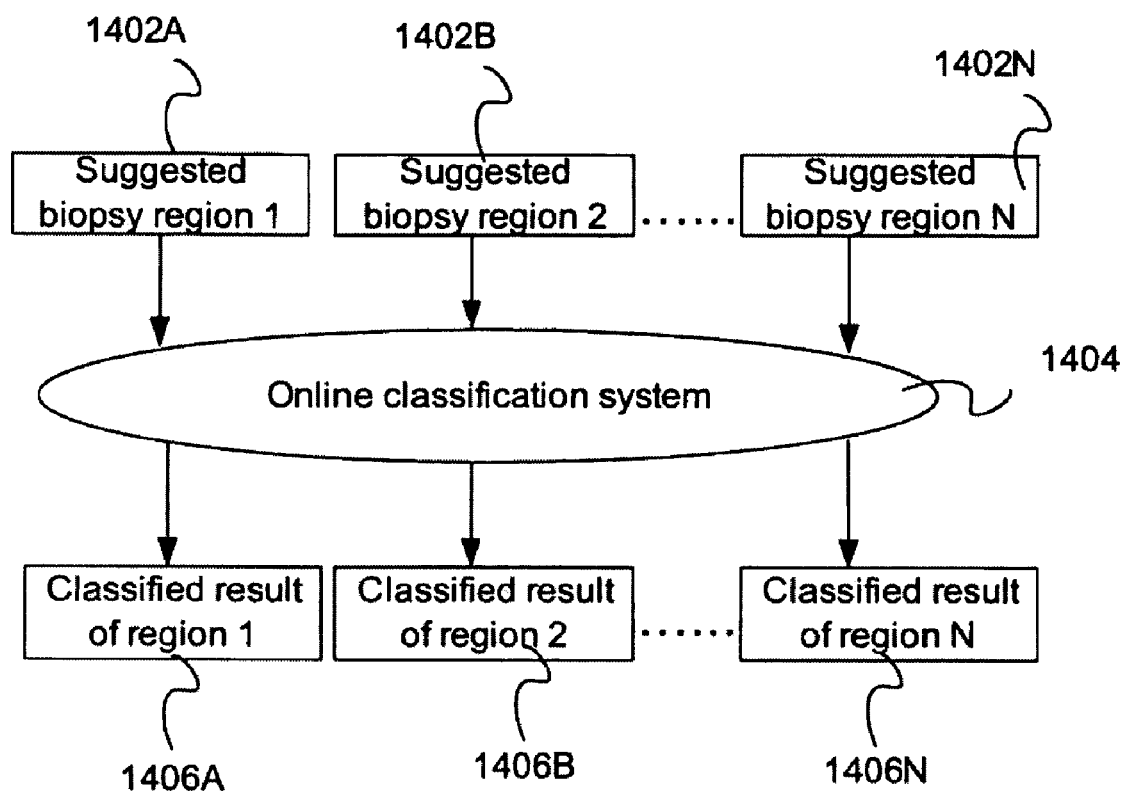
FIG. 14. illustrate a parallel work flow for the online classification system of the second knowledge-based system.

This classification system is an online system and can be used real-time to assist urologists in prostate cancer diagnosis. The workflow may also be designed to enhance the speed of the system. For instance, as illustrated in FIG. 14, parallel processing may be performed on different suggested regions. Suppose the first knowledge-based system identifies N suspicious regions 1402A-N in the prostate and they are regions of interest (ROIs) which are suggested to do biopsy. The online classification system 1404 of the second knowledge-based system does not require the examination of the entire image. It only confirms these suspicious regions and decides whether they are true malignant or not. It is efficient. Instead of confirming them one by one, the N regions are fed into the online classification system 1404 simultaneously, such that there are N parallel classification systems. In this way, N suggested ROIs can be classified and confirmed 1406A-N at the same time to show the urologists the final confirmed biopsy locations.

Figure 15:
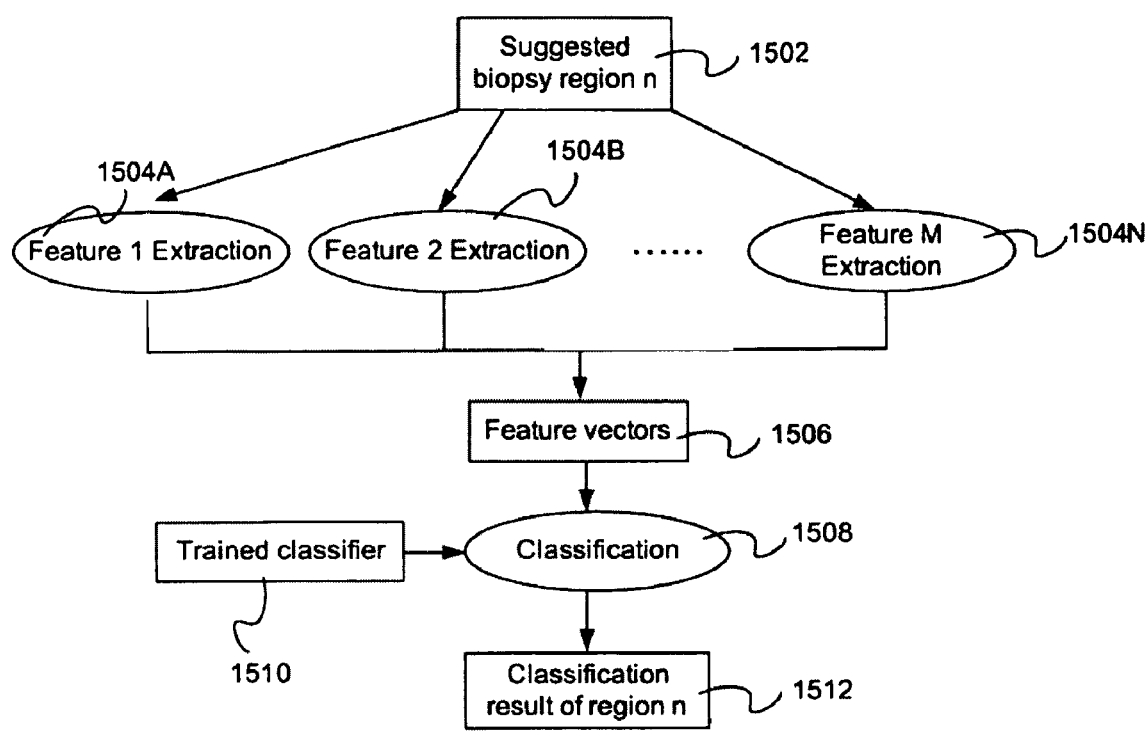
FIG. 15. illustrate a parallel work flow for feature extraction for the online classification system of the second knowledge-based system.

In a further arrangement for speeding processing time (See FIG. 15), feature extraction for each ROI may be performed in parallel. That is, for each suggested biopsy region 1502, M features may be used to describe a ROI. These M features are selected from the feature selection step in the offline model training system. The same M features have been used to train the classifier in the offline system. Then in the online classification system, M features need to be extracted 1504A-M for each ROI 1502. Here a multi-threading technique is applied to extract M features for each ROI. In the system, M parallel filters are applied to compute these M features simultaneously by multi-threading technique. As shown in FIG. 15, in this way, we can save computation time.

Specifically, for Gabor filtering features, multi-resolution Gabor filter is applied instead of traditional Gabor filter. The concept of multi-resolution with parameter selection is used. The computation time can be reduced by diminishing the image size according to several different sets of parameters. After feature extraction, M features are obtained for each ROI, this feature vector 1506 (M dimensional) is used as inputs to the classifier process 1508 within the trained classifier 1510, then the output 1512 (whether it is true malignant or not) can be computed in real time. Since we have N parallel classification systems, the confirmed results of these N regions are known simultaneously.

Finally, the online classification system may be implemented on a GPU based framework, which may speed up computation to a factor of 30 compared with the traditional CPU framework.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

The invention claimed is:

1. A method for use in a computer system associated with a medical imaging device for use in prostate biopsy planning and targeting, comprising:

obtaining an electronic image of a prostate of a patient;
utilizing a predefined deformable prostrate shape model, supported by said computer system, to identify at least one region of interest on said prostate image for potential biopsy, wherein said predefined deformable shape model comprises an average shape of a plurality of prostate images and includes a cancer probability map identifying one or more prostate regions statistically likely to have cancer and wherein utilizing said shape model includes:
deforming the predefined deformable shape model to fit the electronic image of the prostate; and;
identifying said at least one region of interest based on the one or more prostate regions statistically likely to have cancer as deformed to fit the electronic image of the prostate;
utilizing a knowledge based system, supported by said computer system, to examine said region of interest on said prostate image, wherein said knowledge-based system generates an output indicating a desirability of performing biopsy on each said region of interest.

2. The method of claim 1, wherein utilizing said knowledge-based system comprises:
analyzing said region of interest to identify features of interest.

3. The method of claim 2, wherein analyzing comprises:
performing a texture analysis of each said region of interest; and
comparing results of said texture analysis to predetermined classifiers to determine if said region of interest is one of potentially malignant and potentially benign.

4. The method of claim 3, wherein texture analysis is performed on a plurality of regions of interest and said analysis is performed in a plurality of in parallel processing paths.

5. The method of claim 3, wherein comparing results of said texture analysis further comprises:
identifying a plurality of features in a region of interest; and
comparing said features to said predetermined classifiers, wherein comparison of said plurality of features is performed in a plurality of parallel processing paths.

6. The method of claim 3, wherein performing a textural analysis comprises:
extracting at least a first feature vector from said regions of interest and wherein comparing comprises comparing said first feature vector to predetermined feature vectors associated with histological data.

7. The method of claim 6, wherein extracting a first vector comprises extracting at least one of
statistical features;
gradient features;
Gabor filtering features.

* * * * *